United States Patent [19]

Fikentscher et al.

[11] Patent Number: 5,077,426

[45] Date of Patent: Dec. 31, 1991

[54] PREPARATION OF ALPHA-FORMYLAMINO NITRILES

[75] Inventors: Rolf Fikentscher, Ludwigshafen; Michael Kroener, Mannheim, both of Fed. Rep. of Germany

[73] Assignee: BASF Aktiengesellschaft, Ludwigshafen, Fed. Rep. of Germany

[21] Appl. No.: 627,022

[22] Filed: Dec. 13, 1990

[30] Foreign Application Priority Data

Dec. 22, 1989 [DE] Fed. Rep. of Germany ....... 3942576

[51] Int. Cl.$^5$ ............................................ C07C 255/00

[52] U.S. Cl. .................................... 558/452; 546/330; 548/343; 548/505; 548/550; 548/561; 549/13; 549/76; 549/378; 549/476; 549/493; 558/404; 558/430; 558/434; 558/448; 558/449; 558/447

[58] Field of Search ............... 558/452, 447, 449, 448, 558/434, 430, 404; 546/330; 548/343, 505, 550, 561; 549/13, 76, 378, 426, 493

[56] References Cited

U.S. PATENT DOCUMENTS 4,701,546 10/1987 Bewert et al. ...................... 558/445

FOREIGN PATENT DOCUMENTS 0205131 6/1986 European Pat. Off. .
1950280 4/1971 Fed. Rep. of Germany .

OTHER PUBLICATIONS

Justus Liebigs Ann. Chem. 735 (1970) pp. 27-34.

*Primary Examiner*—Bruce D. Gray
*Attorney, Agent, or Firm*—John H. Shurtleff

[57] ABSTRACT

A process for preparing α-formylamino nitriles of the formula Ia

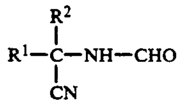

Ia and Ib

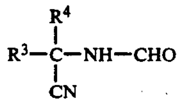

Ib where $R^1$, $R^2$, $R^3$ and $R^4$ are identical or different and each is hydrogen or unsubstituted or substituted, with substituents which are inert under the reaction conditions, aliphatic or heteroaliphatic radicals with 1 to 10, cycloaliphatic or heterocycloaliphatic radicals with 3 to 6, araliphatic radicals with 7 to 12, heteroaraliphatic radicals with 4 to 12, aromatic radicals with 6 to 10 or heteroarometic radicals with 3 to 10 carbon atoms, with the priviso that at least one of $R^1$ and $R^2$ or $R^3$ and $R^4$ is hydrogen, comprises reacting an iminodiacetonitrile of the formula II

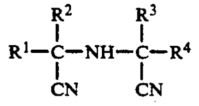

II where $R^1$, $R^2$, $R^3$ and $R^4$ have the abovementioned meanings, with formamide of the formula III

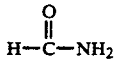

III in the presence of formic acid or with a compound which provides formic acid, in the presence of acids.

7 Claims, No Drawings

PREPARATION OF ALPHA-FORMYLAMINO NITRILES

The present invention relates to a process for preparing α-formylamino nitriles of the formulae Ia

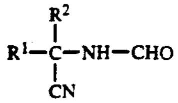

Ia and Ib

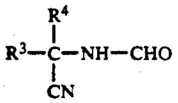

Ib where $R^1$, $R^2$, $R^3$ and $R^4$ are identical or different and each is hydrogen or unsubstituted or substituted, with substituents which are inert under the reaction conditions, aliphatic or heteroaliphatic radicals with 1 to 10, cycloaliphatic or heterocycloaliphatic radicals with 3 to 6, araliphatic radicals with 7 to 12, heteroaraliphatic radicals with 4 to 12, aromatic radicals with 6 to 10 or heteroaromatic radicals with 3 to 10 carbon atoms, with the proviso that at least one of $R^1$ and $R^2$ or $R^3$ and $R^4$ is hydrogen.

U.S. Pat. No. 3,822,306 discloses that α-formylamino nitriles I where in each case one of $R^1$ and $R^2$ or $R^3$ and $R^4$ is not hydrogen can be obtained by acid-catalyzed reaction of the corresponding cyanohydrins IV

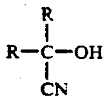

IV (R, R=$R^1$, $R^2$ or $R^3$, $R^4$) with formamide III at from 60° to 180° C. This process is preferably carried out with an excess of from 2 to 3 mol of formamide per mole of cyanohydrin IV.

Although the process of U.S. Pat. No. 3,822,306 gives good results in the preparation of α-formylamino nitriles, for example the nitrile of N-formylalanine V

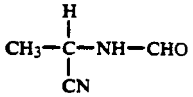

V can be obtained in a yield of 82% of theory in this way, starting from acetaldehyde cyanohydrin, the process did appear to be capable of improvement in some respects. Thus, for example, the preparation of the nitrile of N-formylalanine by this process gave rise, owing to a number of unknown side reactions, to 4 to 6 l of gas per liter of reaction liquid, the gas being essentially composed of a mixture of carbon monoxide and carbon dioxide plus about 5% of hydrogen cyanide, which meant that elaborate safety measures were needed for its disposal. This evolution of gas and the associated bumping makes it difficult to carry out the reaction safely, for which reason the reactor must be equipped with additional safety devices.

As a consequence of the said side reactions, the yield of formylamino nitrile in this process is only 75% of theory based on formamide. In addition, under the reaction conditions the cyano groups of both the formylamino nitrile and the cyanohydrin were partially hydrolyzed by the water of reaction to the carboxamide, which likewise results in losses of yield.

It is an object of the present invention to find a process for preparing α-formylamino nitriles I, i.e. Ia and Ib, which does not have these disadvantages and makes it possible to prepare I economically.

We have found that this object is achieved by a process for preparing α-formylamino nitriles of the formula Ia

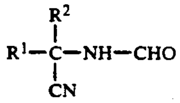

Ia and Ib

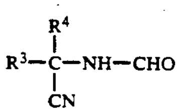

Ib where $R^1$, $R^2$, $R^3$ and $R^4$ are identical or different and each is hydrogen or unsubstituted or substituted, with substituents which are inert under the reaction conditions, aliphatic or heteroaliphatic radicals with 1 to 10, cycloaliphatic or heterocycloaliphatic radicals with 3 to 6, araliphatic radicals with 7 to 12, heteroaraliphatic radicals with 4 to 12, aromatic radicals with 6 to 10 or heteroaromatic radicals with 3 to 10 carbon atoms, with the proviso that at least one of $R^1$ and $R^2$ or $R^3$ and $R^4$ is hydrogen, which comprises reacting an iminodiacetonitrile of the formula II

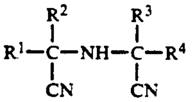

II where $R^1$, $R^2$, $R^3$ and $R^4$ have the abovementioned meanings, with formamide of the formula III

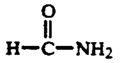

III in the presence of formic acid or with a compound which provides formic acid, in the presence of acids.

The mechanism of the reaction according to the invention has not been examined in detail, but it entails reaction of one molecule of the iminodiacetonitrile II with one molecule each of formamide III and formic acid to give the α-formylamino nitriles Ia and Ib at least formally as shown by equation (1)

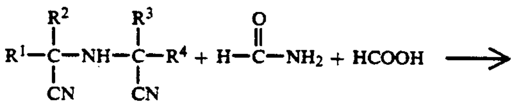

(1)

II III

-continued

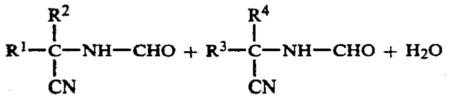

Ia Ib

The stoichiometry of the reaction results in one mole of water per mole of II reacted. Thus, the formic acid in this process acts both as reactant and as acid catalyst.

The formic acid can be used either in the stoichiometric amount or in excess relative to the iminodiacetonitrile II. In general, from 1 to 2 mole of formic acid are used per mole of II, but preferably a slight excess of formic acid, i.e. from 1.001 to 2, advantageously from 1.05 to 1.5 and, especially, from 1.1 to 1.3 mole of formic acid are employed per mole of iminodiacetonitrile II.

In a particularly advantageous embodiment of the process according to the invention, mixtures of formic acid and alkyl formates (HCOOAlk) are used in place of formic acid, in which case the individual components in these mixtures, namely formic acid and alkyl formate, can be added to the reaction mixture separately or together. The added alkyl formate is presumably able to assume the function of the formic acid as reactant so that only catalytic amounts of formic acid are now required in the reaction mixture. This variant according to the invention can be represented purely formally by equation (2):

(2)

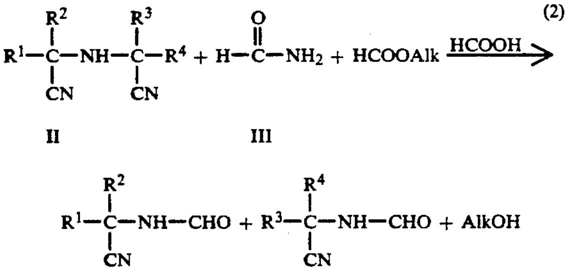

It is possible in principle to use all esters of formic acid to carry out this variant of the process according to the invention. However, for reasons of cost as well as of availability, $C_1$-$C_6$, especially $C_1$-$C_4$, alkyl formates and specifically methyl formate will preferably be used. Mixtures of these formates or, preferably, the individual alkyl formates can be employed.

When alkyl formates are used as reactants, formally 1 mole of the alcohol AlkOH is liberated per mole of iminodiacetonitrile II. The alcohol produced in the reaction can be recovered by distillation during working up of the reaction mixture and can be reused for other purposes. Thus, in this variant of the reaction there is formally no formation of water. Any water which is present in the mixture, whether introduced, for example, by water-containing reactants or produced by reaction in accordance with equation (1) brought about by residual catalytic amounts of formic acid, has no adverse effect on the yield of the reaction, apparently as a consequence of the presence of the alkyl formate, i.e. in the presence of the alkyl formate there is apparently no measurable hydrolysis of the α-formylamino nitriles I in accordance with equation (3).

(3)

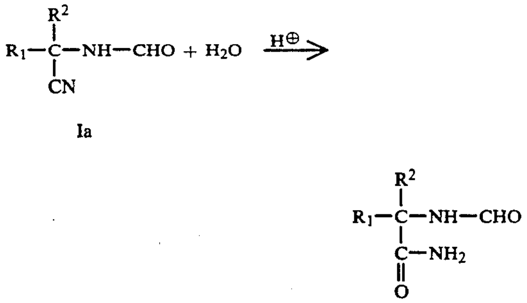

Virtually any ratio of the amounts of alkyl formates and iminodiacetonitrile II is possible. If less than the stoichiometric amount of the alkyl formate is used, a larger proportion of formic acid is required in the reaction mixture to achieve complete conversion of II in accordance with the stoichiometry of equations (1) and (2). When the amount of alkyl formate is stoichiometric or in excess relative to II, generally only catalytic amounts of formic acid are required. The alkyl formates are advantageously employed in amounts of from 1 to 2 mole per mole of iminodiacetonitrile II. In this case, it is generally sufficient to add from 0.01 to 1, preferably from 0.05 to 0.9 and, in particular, from 0.1 to 0.3 mole of formic acid per mole of II for a suitable reaction rate.

When the amount of alkyl formate is stoichiometric or in excess relative to II, the formic acid needed to catalyze the reaction can be replaced by other acids, preferably mineral acids. Preferably used for this purpose are anhydrous mineral acids which have no oxidizing action under the reaction conditions, such as hydrogen chloride, hydrogen fluoride and tetrafluoroboric acid. The relevant mineral acid is usually added in amounts of from 0.01 to 1, preferably from 0.05 to 0.9 and, in particular, from 0.1 to 0.3 mole of acid per mole of II to the reaction mixture.

All variants of the process according to the invention can be carried out with equimolar amounts of formamide and iminodiacetonitrile II, but excess formamide is preferably used. As a rule, from 1.1 to 2.0 mole, preferably from 1.2 to 1.8 mole, of formamide are used per mole of II. Larger excesses are possible.

All variants of the process according to the invention are normally carried out at from 20° to 150° C., advantageously from 60° to 120° C. and, preferably at from 80° to 100° C. All variants can be carried out under atmospheric pressure, but elevated pressure is expedient, especially the autogenous pressure of the reaction system. This procedure is particularly advantageous when low-boiling alkyl formates are used.

Both main variants of the process according to the invention, i.e. in the presence and absence of alkyl formates, can be carried out either batchwise in stirred vessels, preferably in stirred autoclaves, or continuously in tube reactors, or advantageously in pressure-stable stirred vessel cascades. The reaction mixture can be worked up, and the product(s) can be isolated, by conventional methods such as distillation, extraction or crystallization. In the case of distillable products, the discharge from the reactor is preferably worked up by distillation.

The process according to the invention can be used to prepare virtually all α-formylamino nitriles I from the relevant iminodiacetonitriles II. Thus, compounds I, i.e. Ia and Ib, can be prepared advantageously from the iminoacetonitriles II where $R^1$, $R^2$, $R^3$ and $R^4$ are identical or different and each is hydrogen or unsubstituted or substituted, with substituents which are inert under the reaction conditions, aliphatic or heteroaliphatic radicals with 1 to 10, cycloaliphatic or heterocycloaliphatic radicals with 3 to 6, araliphatic radicals with 7 to 12, heteroaraliphatic radicals with 4 to 12, aromatic radicals with 6 to 10 or heteroaromatic radicals with 3 to 10 carbon atoms, with the proviso that at least one of $R^1$ and $R^2$ or $R^3$ and $R^4$ is hydrogen.

$R^1$, $R^2$, $R^3$ and/or $R^4$ can have substituents which are inert under the reaction conditions, such as halogen, $C_1$–$C_4$-alkyl, $C_1$–$C_4$-alkoxy or $C_1$–$C_4$-haloalkoxy. The number of the substituents is not in general critical for the success of the reaction according to the invention, but $R^1$ to $R^4$ normally do not have more than 3 of the said substituents. Aliphatic radicals $R^1$, $R^2$, $R^3$ and/or $R^4$ can be straight-chain or branched. Heteroaliphatic radicals $R^1$, $R^2$, $R^3$ and/or $R^4$ preferably contain oxygen atoms, specifically from 1 to 5 depending on the size of the radical, as hetero atoms, preferably in the form of ether groupings. The heterocycloalkyl, heteroaralkyl and heteroaryl $R^1$, $R^2$, $R^3$ and/or $R^4$ may in general contain 1 or 2 of the hetero atoms nitrogen, oxygen and/or sulfur.

In order to illustrate the range of applicability of the process according to the invention, a number of meanings of $R^1$ to $R^4$ in α-formylamino nitriles Ia and Ib obtainable according to the invention from the corresponding substituted iminodiacetonitriles II follow: hydrogen, methyl, ethyl, propyl, isopropyl, butyl, isobutyl, hexyl, phenyl, benzyl, phenylethyl, phenylpropyl, phenylisopropyl, 4-methylbenzyl, 4-methoxybenzyl, 2,6-dichlorophenyl, 4-chlorobenzyl, 4-hydroxybenzyl, 4-chlorophenyl, cyclopropyl, cyclohexyl, 1-methylcyclopropyl, 2-pyrrolidone-3-ethylene-yl, tetrahydropyran-3-yl, tetrahydrothiopyran-3-yl, 2-pyridyl, 3-furyl, 5-hydroxymethyl-2-furyl, 2-pyrrolyl, imidazole-4-methylene-yl, 3-thienyl and (1H)-indole-3-methylene-yl.

It is also possible to use the process according to the invention to prepare α-N-formylamino nitriles I, i.e. Ia and Ib, where $R^1$ and/or $R^2$ and $R^3$ and/or $R^4$ are alkoxy or polyalkoxy. Examples of α-N-formylamino nitriles which can be obtained advantageously by the process according to the invention are those in which $R^1$, $R^2$, $R^3$ and/or $R^4$ are methoxy, propoxy, hexoxy, methoxyethylene-yl, propoxyethylene-yl, methoxypropylene-yl, ethoxypropylene-yl, propoxypropylene-yl, hexoxypropylene-yl, oxyethylenemethoxy, oxyethylenepropoxy, bis(oxyethylene)methoxy, bis(oxyethylene)ethoxy, bis(oxyethylene)hexoxy, tetrakis(oxyethylene)methoxy and tetrakis(oxyethylene)ethoxy.

The iminodiacetonitriles II used as starting compounds can be obtained, for example, by the process in DE-A 14 93 752 in which the appropriate cyanohydrins IV ($R=R^1$, $R^2$ and/or $R^3$, $R^4$) are reacted with ammonia in accordance with equation (4):

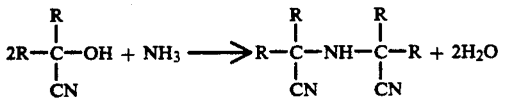

(4)

IV II

As an alternative, the iminodiacetonitriles II can be obtained by reacting a cyanohydrin IV with an α-amino nitrile VI by the process of U.S. Pat. No. 4,543,215, in accordance with equation (5) ($R=R^1$, $R^2$ and/or $R^3$, $R^4$):

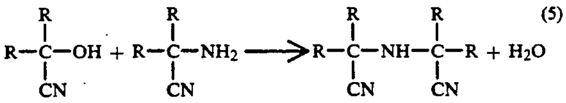

(5)

IV VI II

In this connection, the process of U.S. Pat. No. 4,543,215 is particularly advantageous for preparing iminodiacetonitriles II where $R^1$ and $R^2$ differ from $R^3$ and $R^4$. Since the iminodiacetonitriles II are usually insoluble or only slightly soluble in water, the water produced during their preparation can be substantially removed by simple phase separation before they are used in the process according to the invention.

The residual water content in the iminodiacetonitriles obtained in this way does not usually have an adverse effect on the result of the process according to the invention, especially when alkyl formates are used. It may prove to be advantageous, both when iminodiacetonitriles II containing residual water are used and when water-containing formic acid is used, to increase the amount of alkyl formate employed, to compensate for the water content of the reaction mixture. As a rule, an additional 0.5–2 mole, preferably 1 mole, of alkyl formate is added per mole of water present in the reaction mixture.

The reaction on which the process according to the invention is based has not been disclosed, and it takes place surprisingly smoothly. In addition, surprisingly, not only does the process according to the invention avoid the disadvantages of the process of U.S. Pat. No. 3,822,306, i.e. no gas containing hydrogen cyanide is evolved, and the partial hydrolysis of the formylamino nitriles is suppressed, which means that the yield of I is considerably improved, the process according to the invention is also more economic because the amount of formamide used can be halved. This is apparently due to the function of the formamide in the process according to the invention being partly taken over by the alkyl formate or the formic acid which is more favorable in terms of cost.

The α-formylamino nitriles obtainable according to the invention can be hydrolyzed as described in U.S. Pat. No. 3,822,306 to the corresponding amino acids. In addition, the α-formylamino nitriles obtainable according to the invention can be converted by thermal elimination of hydrogen cyanide by the processes of DE-A 16 68 038 and EP-B 184 074 into the corresponding formylamino alkenes which are used as monomers. For example, the nitrile of N-formylalanine obtainable according to the invention can be pyrolyzed by this process to give N-vinylformamide which is converted by the processes of EP-B 71 050 and EP-A 23 19 01 into basic polymers which are used, for example, as auxiliaries in paper finishing.

EXAMPLES

EXAMPLE 1

Nitrile of N-formylalanine 184.5 g of iminodipropionitrile (1.5 mol; $R^1$, $R^2=R^3$, $R^4=H$, methyl) were mixed with 81 g of formamide (1.8 mol), 108 g of methyl formate (1.8 mol) and 34.5 g of formic acid (0.75 mol) and heated in a stirred autoclave at 90° C. for 7 h. The pressure set up in the autoclave was 2.3 bar. The reactor was then cooled to room temperature and the pressure was released. The discharge from the reactor still contained 8.2 g of unreacted iminodipropionitrile, corresponding to a conversion of 95.6%. The yield of the nitrile of N-formylalanine after working up by distillation was 91.6% based on reacted dinitrile.

EXAMPLE 2

Nitrile of N-formylalanine

A sample of iminodipropionitrile which, apart from 184.5 g of iminodipropionitrile, contained 18 g of water was mixed with 81 g of formamide (1.8 mol), 168 g of methyl formate (2.8 mol) and 34.5 g of formic acid (0.75 mol) and heated at 100° C. in a stirred autoclave for 3 h. A pressure of 4.3 bar was set up in the autoclave. The latter was then cooled to room temperature and the pressure was released. The discharge from the reactor contained 4.9 g of unreacted dinitrile, corresponding to a conversion of 97.3%. The yield of nitrile of N-formylalanine after working up by distillation was 92.5% based on reacted dinitrile.

EXAMPLE 3

Nitrile of N-formylalanine

The reaction mixture was the same as in Example 2 but the reaction was carried out at 90° C. for 7 h. The autogenous pressure in the autoclave was found to be 2.4 bar. The discharge from the reactor was worked up as described in Example 2. Yield: 96.3% (based on reacted dinitrile).

EXAMPLE 4

Nitrile of N-formylalanine 55.4 g of iminodiproprionitrile (0.45 mol) were heated with 34.4 g of formamide (0.75 mol) and 31 g of formic acid (0.67 mol) at 90° C. for 4 h while stirring. The discharge from the reactor was worked up by distillation. Conversion was 99% and yield was 86.7% (based on reacted dinitrile).

EXAMPLE 5

Nitrile of alanine and α-formylaminobutyronitrile 61.7 g of α-methyl-α'-ethyliminodiacetonitrile (0.45 mol; $R^1$, $R^2$: H, methyl; $R^3$, $R^4$: H, ethyl) were heated with 28.4 g of formamide (0.63 mol) and 29 g of formic acid (0.63 mol) at 90° C. for 6.5 h while stirring. The discharge from the reactor was worked up by distillation. Conversion was 98%. The yields of nitrile of N-formylalanine and α-formylaminobutyronitrile based on reacted dinitrile were 88.2 and 90.7% of theory, respectively.

EXAMPLE 6

Nitriles of N-formylglycine and N-formylleucine 75.5 g of α-isobutyliminodiacetonitrile (0.5 mol; $R^1$, $R^2$: H, isobutyl; $R^3$, $R^4$: H, H) were heated with 31.5 g of formamide (0.73 mol) and 32.2 g of formic acid (0.7 mol) at 90° C. for 4 h while stirring. The discharge from the reactor was worked up by distillation. Conversion was 97%. The yields of the nitriles of N-formylglycine and N-formylleucine based on reacted dinitrile were 70 and 82.6% of theory, respectively.

EXAMPLE 7

Nitriles of N-formylalanine and N-formylvaline 75.5 g of α-methyl-α'-isopropyliminodiacetonitrile (0.5 mol; $R^1$, $R^2$: H, methyl; $R^3$, $R^4$: H, ispropyl) were heated with 31.5 g of formamide (0.73 mol) and 32.2 g of formic acid (0.7 mol) at 90° C. for 6 h while stirring. The discharge from the reactor was worked up by distillation. Conversion was 96%. The yields of the nitriles of N-formylalanine and N-formylvaline based on reacted dinitrile were 80 and 90% of theory, respectively.

We claim:

1. A process for preparing an α-formylamino nitrile of the formula Ia

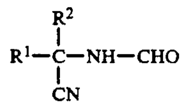

Ia and Ib

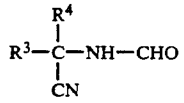

Ib where $R^1$, $R^2$, $R^3$ and $R^4$ are identical or different and each is hydrogen or unsubstituted or substituted, with substituents which are inert under the reaction conditions, aliphatic or heteroaliphatic radicals with 1 to 10, cycloaliphatic or heterocycloaliphatic radicals with 3 to 6, araliphatic radicals with 7 to 12, heteroaraliphatic radicals with 4 to 12, aromatic radicals with 6 to 10 or heteroaromatic radicals with 3 to 10 carbon atoms, with the proviso that at least one of $R^1$ and $R^2$ or $R^3$ and $R^4$ is hydrogen, which comprises reacting an iminodiacetonitrile of the formula II

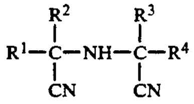

II where $R^1$, $R^2$, $R^3$ and $R^4$ have the abovementioned meanings, with formamide of the formula III

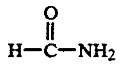

III in the presence of formic acid or with a compound which, in the presence of an acid, provides formic acid.

2. A process as claimed in claim 1, wherein the reaction is carried out in the presence of a $C_1$-$C_6$-alkyl formate as compound providing formic acid, and of formic acid.

3. A process as claimed in claim 1, wherein the reaction is carried out in the presence of a $C_1$-$C_6$-alkyl formate and of a mineral acid.

4. A process as claimed in claim 1, wherein the reaction is carried out at from 20° to 150° C.

5. A process as claimed in claim 1, wherein the reaction is carried out under the autogenous pressure of the reaction system.

6. A process as claimed in claim 1, wherein an iminodiacetonitrile II where $R^1$, $R^2$, $R^3$ and $R^4$ are identical or different and are each hydrogen, $C_1$–$C_{10}$-alkyl, $C_3$–$C_6$-cycloalkyl, $C_7$–$C_{11}$-aralkyl or $C_4$–$C_{11}$-heteroaralkyl, or $C_1$–$C_{10}$-heteroalkyl with 1 to 5 oxygen atoms, and where not less than one of $R^1$ or $R^2$ and $R^3$ or $R^4$ is hydrogen, is reacted.

7. A process as claimed in claim 1, wherein an iminodiacetonitrile II where $R^1$, $R^2$, $R^3$ and $R^4$ are identical or different and are each hydrogen or $C_1$–$C_{10}$-alkyl, and where not less than one of $R^1$ or $R^2$ and $R^3$ or $R^4$ is hydrogen, is reacted.

* * * * *